United States Patent
Oma et al.

(10) Patent No.: US 7,605,919 B2
(45) Date of Patent: Oct. 20, 2009

(54) METHOD AND APPARATUS FOR ANALYZING PARTICLES IN A FLUID

(75) Inventors: Peter Oma, Ottawa (CA); Jarret A. Diggins, Nepean (CA); Antonio J. G. Matias, Ottawa (CA)

(73) Assignee: Brightwell Technologies Inc., Ottawa, Ontario (CA)

( * ) Notice: Subject to any disclaimer, the term of this patent is extended or adjusted under 35 U.S.C. 154(b) by 207 days.

(21) Appl. No.: 11/925,968

(22) Filed: Oct. 28, 2007

(65) Prior Publication Data

US 2008/0100840 A1 May 1, 2008

Related U.S. Application Data

(60) Provisional application No. 60/855,116, filed on Oct. 30, 2006.

(51) Int. Cl.
 *G01N 21/00* (2006.01)
(52) U.S. Cl. .................. 356/339; 356/341
(58) Field of Classification Search .... 356/237.1–243.8
 See application file for complete search history.

(56) References Cited

U.S. PATENT DOCUMENTS

| | | | |
|---|---|---|---|
| 4,338,024 A | 7/1982 | Bolz et al. | |
| 4,393,466 A * | 7/1983 | Deindoerfer et al. | ........ 356/335 |
| 4,830,494 A * | 5/1989 | Ishikawa et al. | ............ 356/336 |
| 5,159,642 A | 10/1992 | Kosaka | |
| 5,426,501 A | 6/1995 | Hokanson et al. | |
| 5,428,451 A | 6/1995 | Lea et al. | |
| 5,619,043 A | 4/1997 | Preikschat et al. | |
| 5,619,333 A | 4/1997 | Staff et al. | |
| 5,835,211 A | 11/1998 | Wells et al. | |
| 5,859,705 A | 1/1999 | Benedetto et al. | |
| 5,880,835 A | 3/1999 | Yamazaki et al. | |
| 6,714,299 B2 | 3/2004 | Peterson et al. | |
| 6,836,559 B2 | 12/2004 | Abdel-Fattah et al. | |
| 7,057,198 B2 * | 6/2006 | Meinhart et al. | ............ 250/573 |
| 7,127,356 B2 | 10/2006 | Nicoli et al. | |
| 7,136,161 B2 | 11/2006 | Nakamura | |
| 7,162,057 B1 * | 1/2007 | Roth et al. | .................. 382/107 |
| 7,167,099 B2 | 1/2007 | Kadwell et al. | |
| 2005/0175508 A1 | 8/2005 | Hill | |

* cited by examiner

*Primary Examiner*—Gregory J Toatley, Jr.
*Assistant Examiner*—Jarreas C Underwood
(74) *Attorney, Agent, or Firm*—Teitelbaum & MacLean; Neil Teitelbaum; Doug MacLean

(57) ABSTRACT

A method and apparatus for analyzing particles in a fluid, such as proteinaceous particles in a pharmaceutical formulation intended for parenteral delivery, are disclosed. The method comprises arranging a fluid to form a wide and shallow stream, acquiring a sequence of magnified still images of the stream, and processing said images, so as to highlight images of particles in the flowing fluid. The apparatus includes a light source, a flow cell, a lens with increased depth of view, a detector array, and a processor for acquiring and processing the images of particles in the fluid stream.

27 Claims, 6 Drawing Sheets

METHOD AND APPARATUS FOR ANALYZING PARTICLES IN A FLUID

CROSS-REFERENCE TO RELATED APPLICATIONS

The present invention claims priority from U.S. provisional patent application No. 60/855,116 filed Oct. 30, 2006, which is incorporated herein by reference.

TECHNICAL FIELD

The present invention is related to particle analysis in fluids, or more precisely, to optical analysis of particle populations in pharmaceutical formulations such as proteinaceous pharmaceutical solutions intended for parenteral delivery.

BACKGROUND OF THE INVENTION

A requirement to detect, size and count individual particles within a particle population suspended in a transparent fluid is frequently encountered in parenteral and general pharmaceutical analysis. Typical populations of interest include aggregates, contaminants, bubbles, and other particles.

Regulatory bodies such as the US FDA apply standards for parenteral injectable and ophthalmic solutions which specify the maximum concentration of particles larger than certain sizes which the solution may contain. The medical reasons for specifying such maximum allowed concentrations is that particulates larger than a certain size, conventionally defined by their equivalent sphere diameter (ESD), can have adverse effects on the patient when injected or placed on the eyes. These standards state that the size of particulates will be measured by a light obscuration instrument or, if the fluid is not suitable for such an instrument, by filtration followed by visual microscopy.

The light obscuration technique consists in passing the particles, one at a time, through an optical beam which then impinges on an optical detector. A threshold is applied to distinguish signals resulting from particles from noise variations. The particle size is determined by comparing, via a calibration table, the reduction in detector signal for each particle with the reduction when polystyrene (PS) spheres of known size are passed through the beam. The system must be recalibrated by the user at regular intervals.

The disadvantages of the light obscuration technique stem from the fact that particles in intravenous solutions are composed materials which are highly transparent and often are far from spherical. As a result, errors in sizing/counting are inevitable. Any optical technique which is employed for particle analysis relies on differences between the particles refractive index and optical absorption and that of the surrounding medium. When these differences are small, the particle may be wholly or partially undetected. In light obscuration, such particles may either not cause a signal reduction which exceeds the threshold for detection or, may cause a reduction which is smaller than that corresponding to a PS calibration sphere having the same ESD.

Another disadvantage of the light obscuration technique is the limited range of particle concentrations that the technique is capable of handling. In light obscuration, if more than one particle is present in the beam, the signal reductions will be added resulting in errors in size and concentration. This limits the maximum concentration of particles which may be present in a sample to approximately 16 thousand per cc, with existing instruments. For samples with unknown concentration, successive dilutions must be carried out until further dilution does not influence the distributions measured.

Measuring size of particulates using visual microscopy also has disadvantages. Visual microscopy is a manual operation, and, therefore, is prone to a subjectivity, error, and fatigue of an operator. Moreover, preparation of samples for microscopic analysis is a lengthy and costly procedure which can only be done by specially trained personnel.

The apparatus described in the present invention is highly tolerant to concentration and refractive index variations of particles being detected in a fluid. The apparatus does not require calibration by an operator, nor does it require a priori information about particle parameters such as size, shape, or transparency. In fact, these parameters can be measured directly for each particle detected. The end user of present invention has an additional benefit of collecting vast information about particle parameter statistics and selecting particle sub-populations based on those statistics, so as to highlight information about particles of interest. In particular, the addition of information on shape parameters is valuable in assessing patient outcomes. Shape and morphology data are also valuable in assisting to identify particle origin for formulation development, stability assessment, process control, quality control, diagnostics and troubleshooting.

The invention allows one to make quantitative measurements which do not rely on operator judgment thereby eliminating human subjectivity and fatigue as a source of error. The skill level, required to operate the apparatus of present invention, is less than that required to perform microscopic analysis. Besides, the invention can be applied to analyze samples in their native form eliminating the cost and time associated with the preparation of microscopic samples. It can also be used to process larger volumes of parenteral formulations over extended periods of time with no degradation in performance.

SUMMARY OF THE INVENTION

In accordance with the invention there is provided a method for analyzing particles in a sample fluid, comprising:
  arranging a sample fluid to form a sample fluid stream traveling in a direction of flow having a depth measuring between 20 microns and 1000 microns, and a width measuring between 25 and 10,000 microns in a direction of width;
  acquiring a sequence of magnified still images of the sample fluid stream, wherein the images are taken in a direction substantially perpendicular to: the direction of flow, and the direction of width of said sample fluid stream; and
  detecting and counting images of particles in said images of the sample fluid stream;
  wherein said detecting includes
  adjusting levels of illumination of said sample fluid stream so as to minimize a noise level present on said still images of sample fluid stream;
  measuring an actual level of illumination used to obtain a particular image of said sample fluid stream, for subsequent processing of such an image;
  subtracting a background image from said images of the sample fluid stream, and forming background-corrected images, wherein said background image is substantially free of images of particles; and
  setting a threshold for the background-corrected images, so as to highlight images of particles present in the background-corrected images of the sample fluid stream.

In accordance with another aspect of the invention there is further provided an apparatus for analyzing particles in a sample fluid, comprising:
a cell including
a fluid inlet port for receiving a stream of the sample fluid in a direction of flow,
a fluid outlet port for outputting the sample fluid stream,
at least two transparent walls parallel to each other separated by a depth of between 20 microns and 1000 microns, and
at least two side walls separated by a width of between 25 and 10,000 microns in a direction of width;
an illumination means for illuminating said cell with light;
an imaging means, coupled to said cell, for acquiring a sequence of magnified still images of the sample fluid stream flowing in said cell, wherein the images are taken in a direction substantially perpendicular to the direction of flow, and the direction of width;
a suitably programmed processor for controlling the illumination means and the imaging means, as well as for detecting and counting images of particles in said images of the sample fluid stream, by
adjusting levels of illumination of said stream so as to minimize a noise level present on said still images of fluid stream,
measuring an actual level of illumination used to obtain a particular image of said fluid stream, for subsequent processing of such an image,
subtracting a background image from each of said images of the sample fluid stream, wherein said background image is substantially free of images of particles, and
setting a threshold to thereby background-corrected images, so as to highlight images of particles present in the background-corrected images of sample fluid stream.

BRIEF DESCRIPTION OF THE DRAWINGS

Exemplary embodiments will now be described in conjunction with the drawings in which.

DETAILED DESCRIPTION OF THE INVENTION

Figure 1:
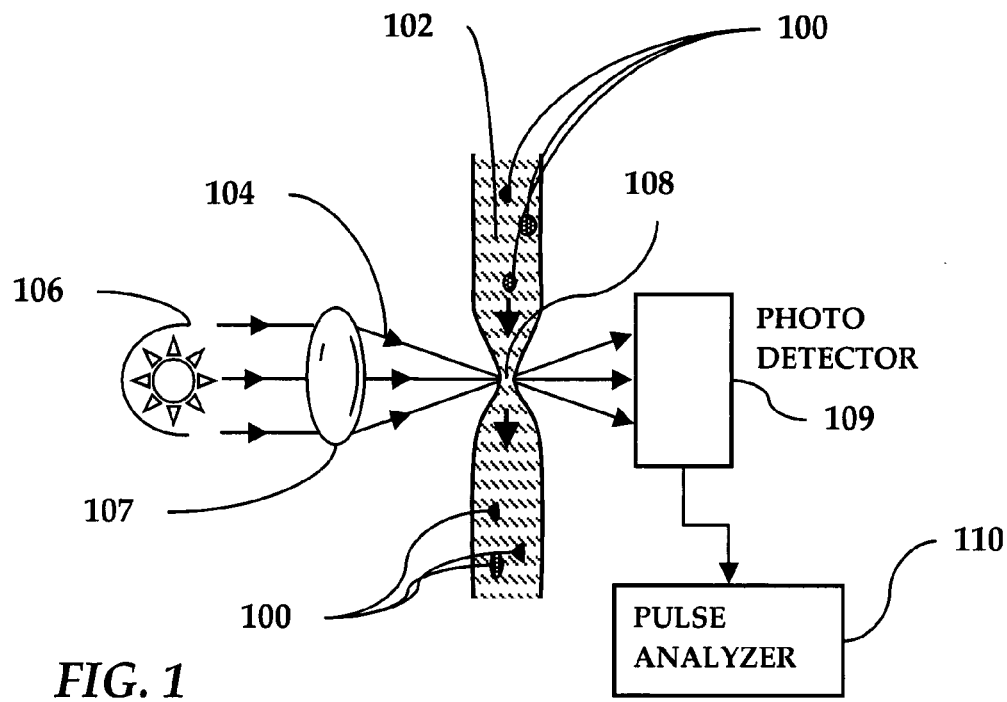
FIG. 1 is a schematic view of a prior art obscuration apparatus.

Referring to FIG. 1, a prior art light obscuration apparatus is shown wherein particles 100 in a fluid 102 are arranged to pass, one by one, through a light beam 104 generated by a light source 106 and focused by a lens 107 onto a measurement area 108. A photodetector 109 is positioned to intercept the light beam 104. A pulse analyzer 110 is coupled to the photodetector 109.

When a particle 100 in a flowing fluid 102 transits the measurement area 108, the light beam 104 is obscured with a resulting change in signal strength at the photodetector 109. This signal change is picked and measured by the pulse analyzer 110. The signal change is then equated to a particle's equivalent circular diameter (ECD) based on a calibration curve created using polystyrene (PS) spheres of a known size. To the extent that particles in intravenous solutions are composed of different materials and are often far from spherical, errors in sizing and counting are unavoidable. Particles which are composed of highly transparent materials can be grossly undersized and, as a result, the concentration of larger particles is underestimated.

Figure 2:
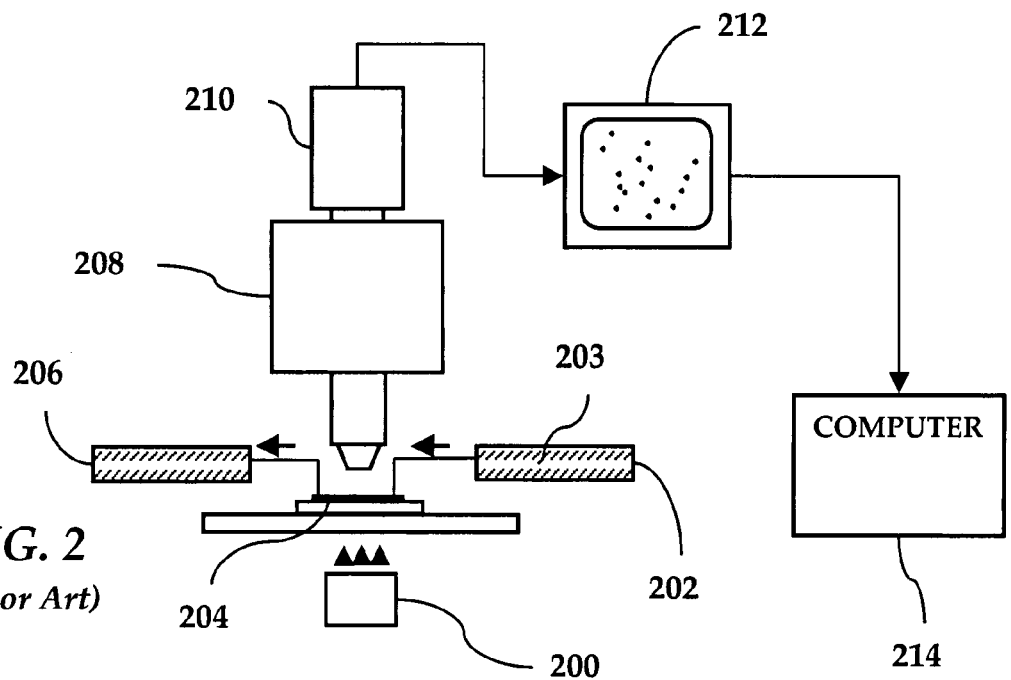
FIG. 2 is a block diagram illustrating a video-microscopic imaging method of prior art.

FIG. 2 illustrates a prior art video microscope imaging and data acquisition system consisting of a light source 200, a fluid supply reservoir 202 containing fluid 203, a measurement cell 204, a fluid output reservoir 206, a conventional light microscope 208, and a CCD camera 210 coupled to a video monitor 212 coupled to a computer 214.

The fluid supply reservoir 202 supplies a fluid 203 to the measurement cell 204. The fluid 203 flows through the cell 204 and is collected into the fluid output reservoir 206. The light source 200 illuminates the measurement cell 204. The conventional bright or dark-field microscope 208 is used to image the cell 204 and the fluid 203 contained therein, onto a CCD camera 210. The CCD camera 210 supplies a video signal to the video monitor 212 which is used to observe particles contained in fluid 203. Said video signal is also supplied to a computer 214 equipped with a frame grabber card (the card is not shown). The computer 214 is used to count particles and calculate concentration of particles in the fluid 203.

While the prior art system of FIG. 2 is capable of counting dense particles in a fluid such as metal colloid particles, it is not suitable for the analysis of proteinaceous particles in parenteral fluids. The particles in parenteral fluids are highly transparent and may not be easy to characterize using a regular microscope, configured either for bright- or dark-field illumination. Besides, a common method of arranging a flow of the fluid 203 by generating a pressure in the reservoir 202 is not appropriate for delicate particles which can break if the fluid stream is not carefully handled. The depth of field in a conventional microscope is small (typically 14 and 4 micrometers for a times 5 and 10 microscope objective respectively). Confining the fluid flow to such a small depth is impractical. If the sample depth is larger than the depth of field, particles which lie wholly or partially outside this field will out-of-focus and enlarged and cannot be accurately measured.

Figure 3:
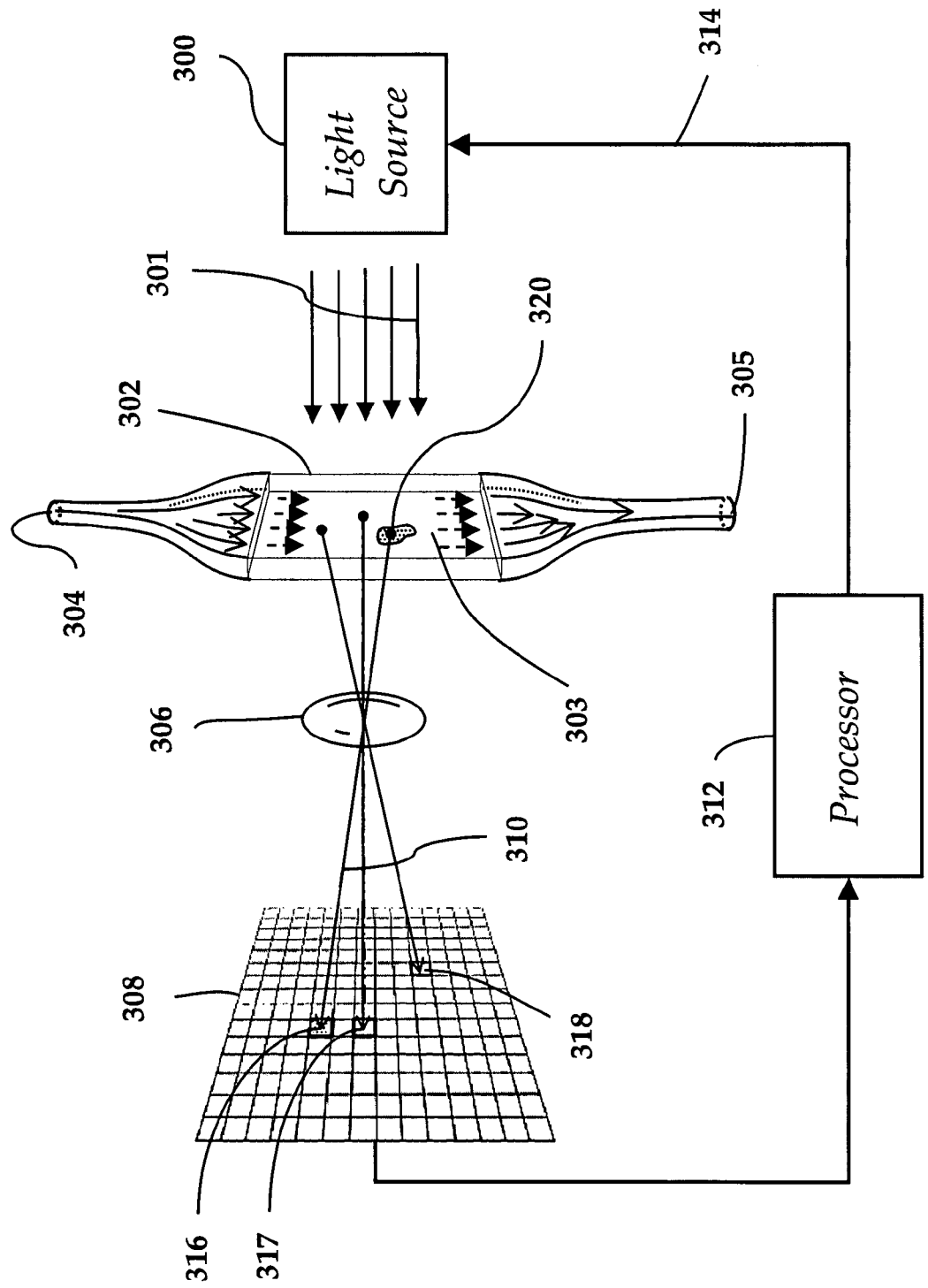
FIG. 3 is a schematic illustrating the method and apparatus of present invention.

Referring now to FIG. 3, an apparatus of present invention is schematically illustrated wherein a light source 300 illuminates a cell 302 containing fluid 303 flowing from inlet 304 to outlet 305. The illuminating light is denoted with arrows 301. An imaging lens 306 having an extended depth of field projects an image of the fluid 303 flowing within the cell 302 onto a detector array 308 as schematically shown by rays 310. The depth of field is such that all images of particles present in the fluid 303 flowing in the cell 302 are in-focus. The detector array 308 is connected to a data processor 312 for processing a digital image obtained by detector array 308 and for adjusting levels of illumination of the cell 302 by the light source 300. The link 314 between the processor 312 and the light source 300 allows for the level of illumination by light source 300 to be precisely controlled by the processor 312. In FIG. 3, three representative pixels of the detector array 308, labeled 316, 317, and 318, are highlighted with the purpose of illustrating a basic image capturing algorithm.

The data collection by the apparatus of FIG. 3 is organized as follows. The value recorded by pixels of the detector array 308, absent any flow cell, following any pulse of illumination (1 pulse per frame) depends on the pixels' intrinsic noise and noise variation and on the optical energy in the pulse (this pulse energy also varies because of device noise and pulse duration noise). When the cell 302 and fluid 303 are present, the signal of pixels 316, 317, and 318 of the detector array 308 shown in FIG. 3, will be reduced as a result of absorption and reflection. If artifacts, such as stuck particles from previous runs, scratches or dirt, are present, those pixels which lie wholly or partially within the images of these artifacts will see reduced optical energy.

For maximum sensitivity and accuracy of operation the system compensates for these effects. Prior to each sample run, a particle free fluid is passed through the cell 302, and a series of frames are recorded.

Firstly, to minimize noise effects, it is desirable to operate the systems such that, independent of the optical absorption of the sample fluid 303, a pixel of the array 308, e.g. pixel 316, 317, or 318, will always receive approximately the same average illumination from frame to frame. In order to provide this, the average optical energy detected by pixels of the array 308 in the series of pulses is used by the processor 312 to derive a control signal. This control signal is sent through the link 314 and is used to adjust the average illumination pulse energy generated by the light source 300 to achieve near-constant illumination of the array 308.

Secondly, in order to compensate for changes in the optical energy between different light pulses, the relative energy in every light pulse is calculated by recording the values seen by pixels of the array 308. This is used to subtract the effects of pulse energy variations in all pixel measurements, in both background compensation and sample measurements.

Thirdly, in order to compensate for artifacts, the average value measured by each pixel for the particle free frames is recorded.

The combination of these steps allows the expected value of each pixel of the array 308, in the absence of a particle image, to be accurately predicted. If the pixel lies wholly or partially within a particle image, the pixel will not show this expected value. For example, the pixel 316 lies within an image of a particle 320 in the flow of the fluid 303. Because of this, the signal of pixel 316 will be reduced. On the other hand, the values of pixels 317 and 318 will not be reduced, since these pixels do not lie on a particle image. If the actual value and the expected value differ by more than a predetermined threshold amount (typically 4%) and the pixel 316 is connected to a minimum number (typically 9) of additional pixels which also exceed the threshold condition, the software assumes that the pixel 316 lies within an image of the particle 320. The requirement for a minimum number of connected pixels reduces random noise and sets the lower limit for particle measurement.

A number of modifications of the apparatus of FIG. 3 can be envisioned by those skilled in the art. For example, a 10-bit high-resolution charge-coupled device (CCD), or complementary metal-oxide-semiconductor (CMOS) sensor can be used as the detector array 308. A regular microscope objective with an increased depth of field or a specially designed lens can be used to image the fluid stream onto the detector array. Further, it can be advantageous to use a variable magnification lens for imaging particles of widely ranging size. For example, ×5, ×10, ×20, and ×50 microscope objective set, arranged on a turret, or a zoom lens can be used. Any other imaging means which can be connected to a computer, such as a digital camera or a video camera capable of acquiring still images, can also be used in the apparatus of present invention. Finally, a flash lamp, an LED, a laser, or any other illumination means providing light detectable by a detector array, can be employed as a light source 300.

It is also understood that FIG. 3 can be used to describe an associated method of present invention which is particularly valuable when applied for analysis of highly transparent proteinaceous particles in parenteral fluids. Such a method constitutes an integral part of present invention.

Figure 4:
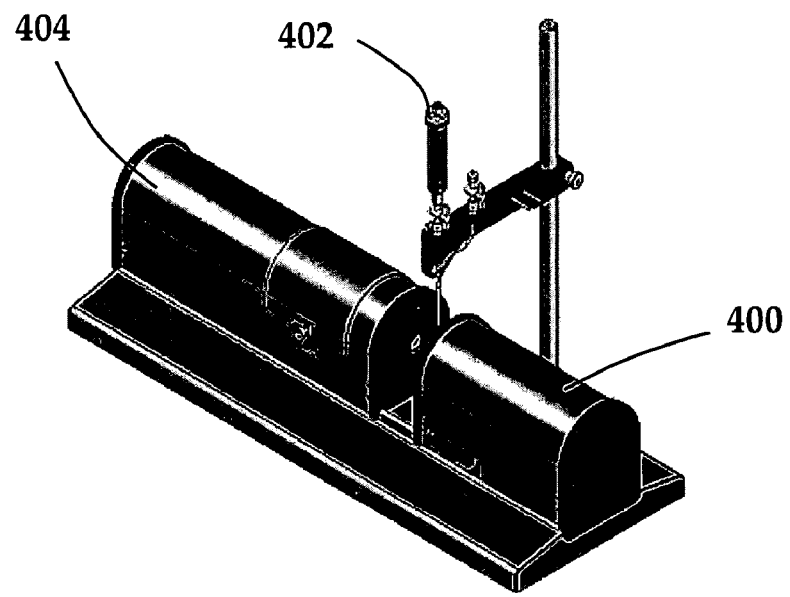
FIG. 4 is an illustration showing appearance of a sampling system of the apparatus of present invention.

Referring now to FIG. 4, an isometric view of a sampling system of the apparatus of present invention is shown wherein a light source 400, fluid supply reservoir 402, and imaging unit 404 are visible on the Figure.

Figure 5:
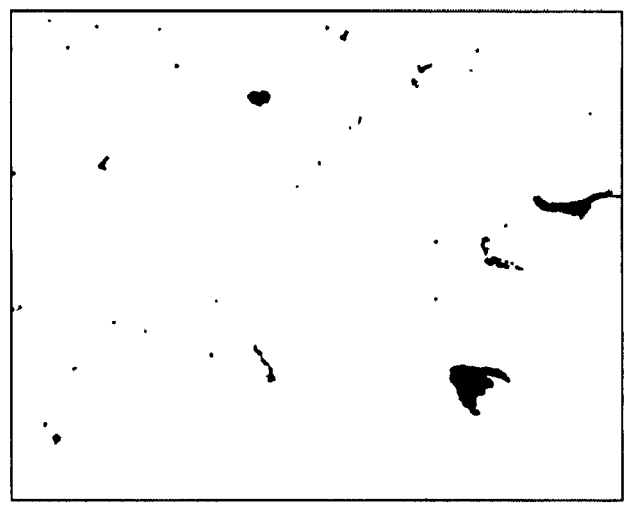
FIG. 5 depicts a typical still image of a fluid stream containing particles in the stream.

On FIG. 5, a typical image frame of a parenteral fluid containing proteinaceous particles is shown. The contrast enhancement technique, described above, was used to automatically acquire this image which would be very difficult to obtain by adjusting a conventional microscope such as the one shown in FIG. 2.

Figure 6A:
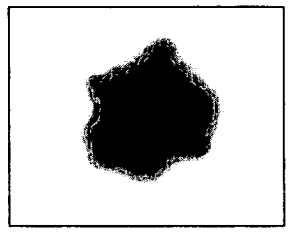
FIGS. 6 A, B, C are the images of individual particles before and after thresholding applied to the images.
Figure 6A:
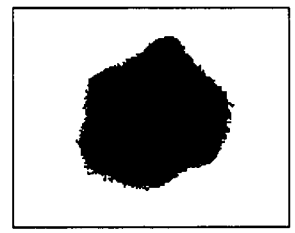
Figure 6B:
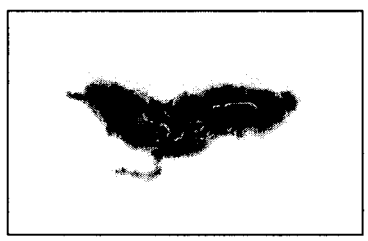
Figure 6B:
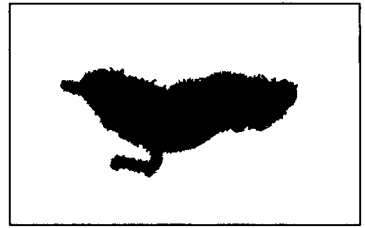
Figure 6C:
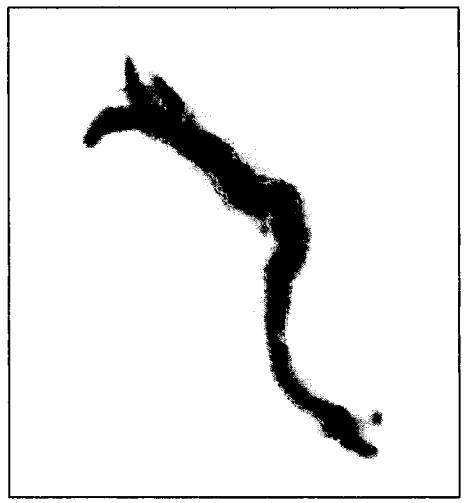
Figure 6C:
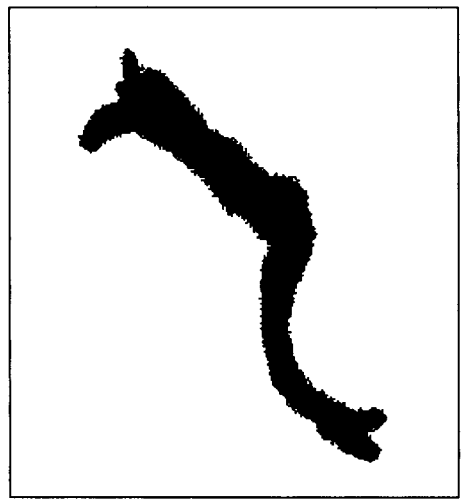

FIGS. 6A, 6B, and 6C further illustrate the advantage of the apparatus and method of present invention in its application to measuring Feret's diameter of various proteinaceous particles found in a sample of parenteral fluid. Feret's diameter is an effective parameter for distinguishing the particles based on their maximum dimension. Images on the left are the grayscale images as seen in the instrument while the images on the right are binary representations of the particles after applying thresholding procedure as described above. FIG. 6A shows a particle with ECD=102.13 microns and Feret's diameter of 113.88 microns. In FIG. 6B, a more elongated, but less dense particle is shown characterized by ECD=120.88 microns and Feret's diameter of 237.88 microns. In FIG. 6C, a highly elongated and transparent particle having ECD of 113.13 micron and Feret's diameter of 339.63 microns is shown. Because the light obscuration technique of FIG. 1 can only compare the signals received from real particles with those from PS spheres, particles are perceived as uniform spheres and particle size expressed in equivalent circular diameter. As one can see by comparing left and right images on FIGS. 6A, 6B, and 6C, this assumption is misleading and particles vary widely in shape and uniformity.

In contrast to the obscuration method, the method of present invention, which we call "Micro-Flow Imaging", or MFI, can be applied to provide an image of each particle detected. Such images can be observed by the user and analyzed by the system software to provide quantitative information on particle morphology. Measurement parameters, which include Feret's Diameter, area, perimeter, transparency and circularity, aspect ratio or any other morphological parameter may be employed to create graphs and scatter plots which characterize the observed particle population. Known artificial intelligence techniques may be employed to identify similar particles directly from the pixel data.

Figure 7:
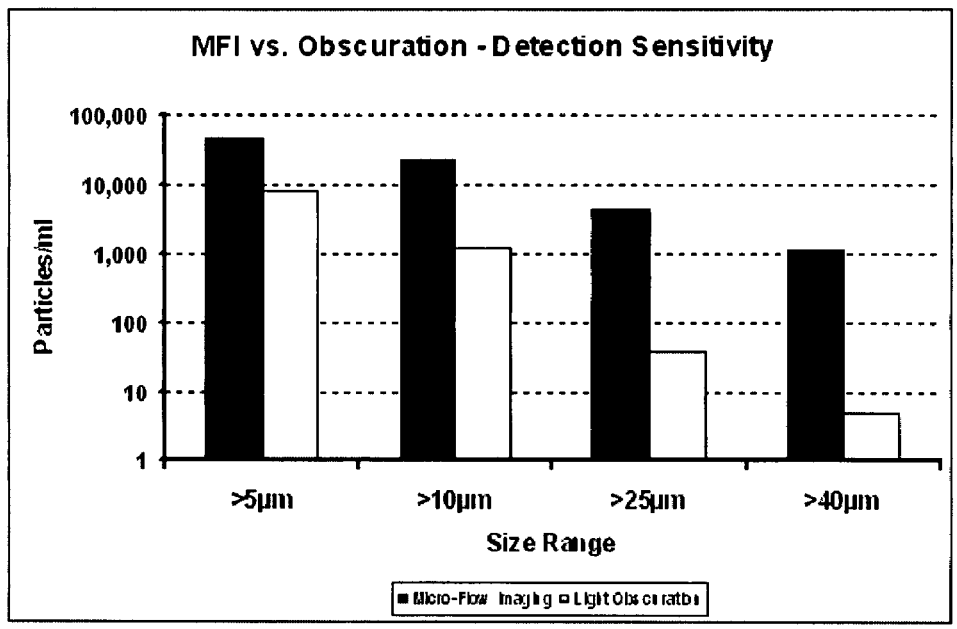
FIG. 7 depicts a result of an experimental comparison of the detection sensitivity of the method of present invention and the prior-art obscuration method.

On FIG. 7, a comparison of measured concentrations of proteinaceous particles in a parenteral fluid is illustrated, wherein the MFI was benchmarked against the light obscuration method. In this Figure, a particle count is plotted vs. size range of the particles detected. It was confirmed by direct microscopic observations that the measurements performed using light obscuration method grossly underestimate concentrations of larger particles. For example, concentrations of particles larger than 40 microns were underestimated in the light obscuration measurements by over 2 orders of magnitude.

The direct, pixel-based imaging technique employed in MFI makes no assumptions of particle material type. Provided the presence of a particle results in sufficient contrast relative to the surrounding suspension fluid, the particle will be accurately sized. No calibration by the user is required. In order to explore the material dependence of parameter measurements, MFI has been evaluated with unstained and stained PS beads and beads of borosilicate glass, as shown below.

Figure 8:
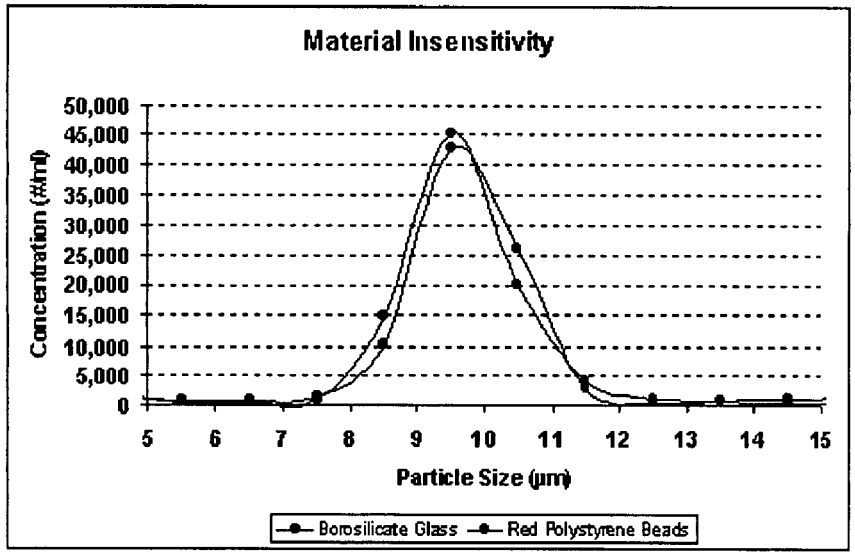
FIG. 8 illustrates an experimental result of using apparatus of present invention to compare concentrations of particles with different transparency.

The results illustrated in FIG. 8 compare measurements of PS beads which were stained red and nearly transparent borosilicate glass beads (both nominally sized at 10 μm). Despite the widely different optical properties of the two types of beads, the sizing results (concentration vs. particle size) are almost identical. Note that these samples were not National Institute of Standards and Technology (NIST)-traceable.

This relative material-insensitivity demonstrates that MFI is well suited for the heterogeneous populations commonly found in intravenous solutions.

Figure 9:
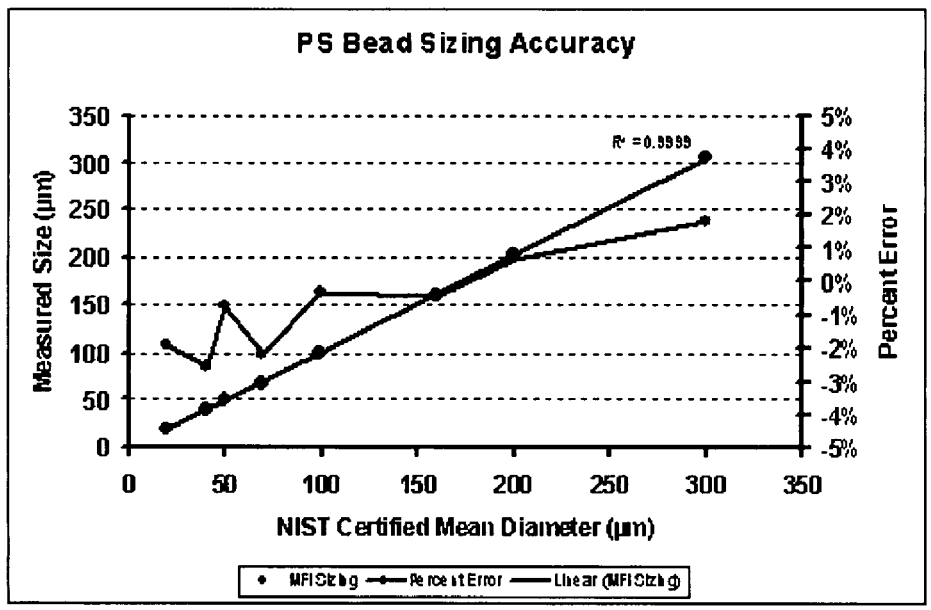
FIG. 9 is a summary diagram illustrating the measured sizing accuracy of NIST traceable particles using the apparatus of present invention.

Turning now to FIG. 9, a result of experimental evaluation of PS beads sizing is shown wherein a measured PS bead size is plotted against NIST certified mean diameter of the beads, said diameter ranging from 0.75 to 400 microns. One can see by looking at the right vertical axis of the plot in FIG. 9 that the error of beads sizing does not exceed +−3%.

Figure 10:
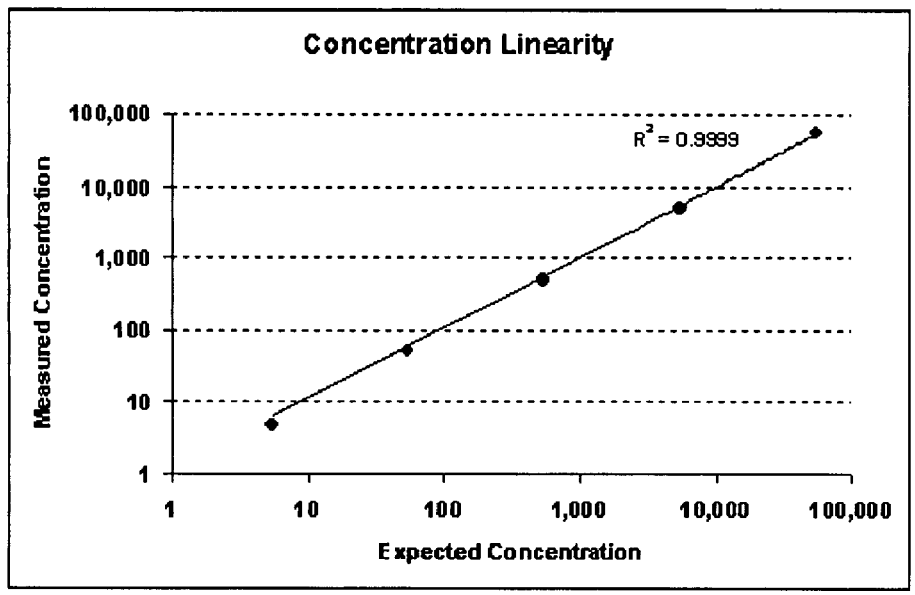
FIG. 10 depicts experimental result of using the apparatus of present invention to measure particle concentrations in a succession of samples obtained by dilution.

On FIG. 10, the results of MFI measurements are shown wherein a 10-fold dilution series were carried out with 10 microns PS bead size standards. In FIG. 10, the vertical and horizontal axes denote the measured and the expected concentration values in particles per ml. An excellent linearity is observed across four orders of magnitude of measured concentration of the beads.

An important characteristic of an instrument is the sampling efficiency defined as the ability of an instrument to analyze 100% of the sample quantity which is drawn through the instrument. For many particle analysis applications where ample sample material is available, this is not a critical parameter. Provided that the quantity actually analyzed by the instrument is known, particle concentrations can be readily calculated. However, in current methods for the analysis of parenterals, limited sample volumes are drawn from production lots. These volumes are determined by the required statistical accuracy and assume that close to 100% of particles contained within these sample volumes are analyzed. In the obscuration method, 100% of the sample fluid passes through the optical beam. Every particle in this fluid can thus provide an obscuration signal reduction and, provided this reduction exceeds a threshold, this reduction can be translated as a particle size. In contrast, the micro-flow imaging examines successive frames taken of a planar flow of sample. To the extent that particles pass through the flow cell between successive frames or pass through the flow cell beside the field of view (FOV), they will not be imaged. Loss of particles by these mechanisms will result in a sampling efficiency of less than 100%. A further challenge results from the fact that the flow of fluids through narrow channels such as those employed in the MFI flow cell has a parabolic velocity profile such that the fluid close to the wall is substantially stationary with that most distant from the walls having the maximum velocity. The flow velocity of particles of finite size in these fluids depends on the velocity of the surrounding fluid and will be slowest close to the walls which define the flow channel.

To maximize sampling efficiency, it is desirable that the frame capture rate and fluid flow velocity be selected so that successive frames record sequential sections of the flow which have very small gaps between them. If the frames overlap, a given particle may be imaged and counted in more than one frame. This situation is called "oversampling". Still, because the flow velocity is non-uniform, a compromise must be selected between oversampling and the sampling efficiency.

The number of particles which may pass undetected beside the FOV may be reduced by reducing the width of the flow channel so that it equals or is less than the FOV. However, this means that the FOV will include the edges of the flow cell where particles have the lowest velocities. To avoid double counting these slow particles, the frame rate must be reduced to a value such that a substantial amount of fluid may pass between frames at the centre of the flow cell.

Based on laboratory studies, a combination of frame rate, average fluid flow velocity, field of view and flow cell channel width have been determined which permit a minimum of 85% of particles larger than 2.5 microns present in the sample to be analyzed.

An alternative technique to address the issue of fluid velocity gradients is the use of a sheathed flow cell. In such a flow cell, the sample flow is surrounded either on two or on all sides by a flow of a particle free sheathing fluid having similar flow properties. The thickness of the sheathing is designed such that the sample flow is confined to a region close to the centre of overall parabolic flow profile in the flow cell where the flow velocity variation is small (for example 10%). Besides oversampling/double counting prevention, the technique of sheathing a flow of sample fluid has an additional important advantage of preventing loose proteinaceous aggregate particles from breaking up in the areas of significant flow velocity gradients.

An additional parameter which is important in the design of the system is minimizing dead-volume in the fluidic system and flow cell. Dead volume is any volume outside the main flow where the fluid is not forced to move at or near the average flow velocity. Any particles which are carried into such dead-volumes may reside there and not be carried into the measurement volume.

Particles observed in an MFI frame may also lie only partially within the FOV with only part of the particle forming an image on the pixels. Since particle size is determined by counting the number of pixels in the particle image, such a particle will be undersized. A sub-windowing algorithm has been developed where the window within which particles are counted and sized is made smaller than the total frame captured. For particles which overlap the edge of this sub-frame, the correct size is determined by counting the additional pixels within the particle image which lie outside the sub-window.

It is required that instruments for characterizing parenteral and ophthalmic fluids can measure particles with sizes up to 300 microns. Such large particles (when composed of the typical materials used to fabricate calibration particles) are not readily aspirated into the flow cell. In other words, the flow velocity is not sufficient to overcome their weight and suck them up. If very high rates of aspiration are employed to overcome this problem, large particles can shear into fragments and thus be undercounted. To address this problem, a gravity assisted sample introduction method has been developed.

Particles found in parenteral and ophthalmic fluids may be highly transparent. Additional microscopy techniques can be employed for gaining further information on the particles and their material composition. These might include illumination and detection at specific wavelengths which maximize or minimize optical absorption, illumination with multiple wavelengths, phase contrast, differential interference contrast, measurement of polarizing effects and fluorescence, use of contrast enhancing optical stains or combinations of these techniques.

An emerging requirement for parenteral drug analysis is to detect and measure very low concentrations of large (visible) particles in the presence of high concentrations of smaller particles. The source of these large particles can include contamination and formulation instability.

At very low concentrations of particles such as 1 particle per ml, most fluid stream images obtained with MFI will appear particle free. The resulting concentration in this case can be calculated by dividing the total amount of particles detected by total volume of the fluid imaged, or, in other words, by averaging concentrations calculated from multiple images acquired.

Table 1 and Table 2 are the results of experiments for the measurement of low concentration suspensions of NIST-traceable, 200-micron PS beads. The first test, summarized in Table 1, used a concentration of ~20 particles per ml created by manually counting and suspending 110 particles into 5 ml of filtered water. The second test, summarized in Table 2, used a concentration of 1 particle per ml created by mixing 5 particles into 5 ml of filtered water.

TABLE 1

Low Concentration Measurement (20 Particles/ml)

| Parameter/Count per 5 ml | R1 |
|---|---|
| Sample | 110 |
| MFI Count (particles >40 μm) | 92 |
| Glassware Count (did not enter the system for analysis) | 16 |
| Image Verification Count (manual verification of stored images | 79 |
| % Recovery - based upon Image Verification | 72% |

TABLE 2

Low Concentration Measurement (1 Particle/ml)

| Parameter/Count per 5 ml | R1 | R2 | R3 | R4 |
|---|---|---|---|---|
| Sample | 5 | 5 | 5 | 5 |
| Count (particles >40 μm) | 7 | 26 | 5 | 5 |
| Image Verification Count | 5 | 5 | 3 | 5 |
| % Recovery (Image Verification) | 100% | 100% | 60% | 100% |

Note 1: R1 and R2 contained additional particles which were shown by image analysis to result from contamination during sample preparation and handling.

Particles may be lost either by lodging in the glassware and tubing or by having passed through the flow cell outside the field of view where the frame is captured. These initial results demonstrate that MFI is capable of reliably detecting very low concentrations of large particles. The value of stored image analysis in providing a method of verifying the analysis and diagnosing unexpected results is also demonstrated.

We claim:

1. A method for analyzing particles in a sample fluid, comprising:
   arranging a sample fluid to form a sample fluid stream traveling in a direction of flow having a depth measuring between 20 microns and 1000 microns, and a width measuring between 25 and 10,000 microns in a direction of width;
   acquiring a sequence of magnified still images of the sample fluid stream, wherein the images are taken in a direction substantially perpendicular to: the direction of flow, and the direction of width of said sample fluid stream; and
   detecting and counting images of particles in said images of the sample fluid stream;
   wherein said detecting includes
   adjusting levels of illumination of said sample fluid stream so as to minimize a noise level present on said still images of sample fluid stream;
   measuring an actual level of illumination used to obtain a particular image of said sample fluid stream, for subsequent processing of such an image;
   subtracting a background image from said images of the sample fluid stream, forming background-corrected images, wherein said background image is substantially free of images of particles; and
   setting a threshold for the background-corrected images, so as to highlight images of particles present in the background-corrected images of the sample fluid stream.

2. A method of claim 1, wherein the sample fluid is a pharmaceutical formulation.

3. A method of claim 2, wherein the pharmaceutical formulation is a protein based drug formulation for parenteral delivery.

4. A method of claim 1, further comprising a step of collecting information on any one or more particle parameters selected from the group consisting of: count, size, shape, transparency, equivalent sphere diameter, perimeter, circularity, aspect ratio and Feret's diameter, of said images of particles in the magnified images of the sample fluid stream.

5. A method of claim 4, further comprising a step of verifying particle parameter information by observing images of the sample fluid stream on a video or digital monitor.

6. A method of claim 5, further comprising a step of filtering particle parameter information comprising:
   selecting at least one target particle image;
   determining any one or more of target particle parameters of said target particle image;
   setting a maximum allowable deviation for any one or more of said target particle parameters of said target particle image; and
   removing particle images from the images of the sample fluid stream, wherein said particle images have associated particle parameters deviating from respective target particle parameters of the target particle image by no more than a predetermined maximum deviation.

7. A method of claim 5, further comprising a step of filtering particle parameter information comprising:
   selecting at least one target particle image;
   determining any one or more of the target particle parameters of said target particle image;
   setting a maximum allowable deviation for any one or more of said target particle parameters of said target particle image; and
   removing particle images from the images of the sample fluid stream, wherein said particle images have associated particle parameters deviating from respective target particle parameters of the target particle image by no less than the maximum predetermined deviation.

8. A method of claim 1, further comprising a step of filtering particle information comprising:
   observing images of the sample fluid stream on a video or digital monitor;

selecting at least one target particle image on at least one of said images of the sample fluid stream;

using artificial intelligence techniques to identify particle images present in the images of the sample fluid stream, wherein said particle images are similar to the at least one target particle image.

9. A method of claim 1, further comprising a step of calculating a concentration of the particles in the sample fluid, said step comprising dividing a total particle count in an image of the sample fluid stream by a volume of the sample fluid captured on the image of the sample fluid stream, wherein said volume is determined by multiplying a total geometric area captured on the image by the depth of the sample fluid stream captured on the image.

10. A method of claim 1, wherein said sample fluid stream is arranged to pass inside a cell having at least four walls, and wherein the sample fluid stream within said cell is surrounded with a sheath fluid stream of a sheath fluid flowing between the sample fluid stream and at least two of said walls of the cell so as to reduce a sample fluid velocity gradient across the sample fluid stream.

11. A method of claim 1, wherein said sample fluid stream is arranged to pass inside a cell having at least four walls, and wherein said walls of the cell are smoothly shaped, so as to avoid formation of dead areas of the sample fluid stream, wherein said dead areas have a flow pattern capable of trapping particles present in the sample fluid.

12. A method of claim 1, wherein a flow of the sample fluid is assisted by gravity.

13. A method of claim 1, wherein a flow velocity of the sample fluid ranges from 0.05 mL to 20 mL per 1 min.

14. A method of claim 1, wherein the combination of the width of the sample fluid stream, a frequency of acquiring the still images, and a velocity of the fluid stream is chosen so as to enable not less than 85% of the particles larger than 2.5 microns, present in the sample fluid, to be detected and counted.

15. A method of claim 1, further comprising a step of collecting information related to size and shape of particles comprising:

defining a counting area within one of the images of the fluid stream, wherein said image consists of pixels and has a total area, and wherein the counting area consists of pixels and has a boundary consisting of boundary pixels, and wherein said counting area occupies between 50% and 90% of the total pixel count of the image; and determining size and shape of particle images in the counting area;

wherein, for a particle image containing at least one of said boundary pixels, the information about size and shape of the particle is collected by analyzing the particle image containing pixels outside of the counting area.

16. A method of claim 9, wherein at least two still images of the sample fluid stream are taken in a succession, and at least two first and second values of concentration are determined from the respective images, and the final concentration value is determined by averaging the at least two values of concentration.

17. A method of claim 1, wherein different magnification set-points are available to suit desired particle sizes.

18. A method of claim 1, wherein the images of particles, present on the images of the sample fluid stream, are in-focus.

19. A method of claim 1, wherein said still images of the sample fluid stream are enhanced by using at least one contrast enhancing method selected from the group consisting of phase contrast, differential interference contrast, polarization contrast, fluorescence, staining and alternative wavelength illumination.

20. An apparatus for analyzing particles in a sample fluid, comprising:

a cell including a fluid inlet port for receiving a stream of the sample fluid in a direction of flow, a fluid outlet port for outputting the sample fluid stream, at least two transparent walls parallel to each other separated by a depth of between 20 microns and 1000 microns, and at least two side walls separated by a width of between 25 and 10,000 microns in a direction of width;

an illumination means for illuminating said cell with light;

an imaging means, coupled to said cell, for acquiring a sequence of magnified still images of the sample fluid stream flowing in said cell, wherein the images are taken in a direction substantially perpendicular to the direction of flow, and the direction of width;

a suitably programmed processor for controlling the illumination means and the imaging means, as well as for detecting and counting images of particles in said images of the sample fluid stream, by, adjusting levels of illumination of said stream so as to minimize a noise level present on said still images of fluid stream, measuring an actual level of illumination used to obtain a particular image of said fluid stream, for subsequent processing of such an image, subtracting a background image from each of said images of the sample fluid stream, wherein said background image is substantially free of images of particles, and setting a threshold to thereby background-corrected images, so as to highlight images of particles present in the background-corrected images of the sample fluid stream.

21. An apparatus of claim 20, wherein said walls of the cell are smoothly shaped, so as to avoid formation of dead areas of the sample fluid stream, wherein said dead areas have a flow pattern capable of trapping particles present in a fluid.

22. An apparatus of claim 20, wherein said imaging means have large enough depth of focus to keep in-focus all images of particles in a fluid between the transparent walls.

23. An apparatus of claim 20, further comprising a video monitor for visual confirmation of results of detecting and counting of the images of particles in the images of the sample fluid stream.

24. An apparatus of claim 20, wherein said cell further comprises a sheath fluid inlet port for providing a sheath fluid stream, said inlet port arranged so as to surround the sample fluid stream with the sheath fluid stream flowing between the sample fluid stream and at least two of the walls of the cell.

25. An apparatus of claim 20, further comprising a sample fluid supply means coupled to the fluid inlet of the cell and located higher, with respect to gravity, than the fluid inlet of the cell, so as to assist a flow of the sample fluid in the cell.

26. An apparatus of claim 20, wherein said imaging means include a variable magnification lens.

27. An apparatus of claim 20, wherein said imaging means include at least one of phase contrast microscope, differential interference contrast microscope, polarization contrast microscope, fluorescence microscope, and a microscope with alternative wavelength illumination.

* * * * *